US010369267B2

(12) United States Patent
Norman et al.

(10) Patent No.: US 10,369,267 B2
(45) Date of Patent: Aug. 6, 2019

(54) SURGICAL FLUID MANAGEMENT SYSTEM (71) Applicant: MEDTRONIC XOMED, INC., Minneaplis, MN (US)

(72) Inventors: Gerould W. Norman, Minneapolis, MN (US); Charles F. Scott Carpenter, Minneapolis, MN (US); Michael L. Koltz, Minneapolis, MN (US); Stephen R. Viviano, Minneapolis, MN (US)

(73) Assignee: MEDTRONIC XOMED, INC., Jacksonville, FL (US)

(*) Notice: Subject to any disclaimer, the term of this patent is extended or adjusted under 35 U.S.C. 154(b) by 583 days.

(21) Appl. No.: 15/053,375

(22) Filed: Feb. 25, 2016

(65) Prior Publication Data
US 2016/0166758 A1    Jun. 16, 2016

Related U.S. Application Data (62) Division of application No. 12/196,777, filed on Aug. 22, 2008, now Pat. No. 9,289,541.

(51) Int. Cl.
*A61M 1/00* (2006.01)
*A61M 3/02* (2006.01)
(Continued)

(52) U.S. Cl.
CPC ............ *A61M 3/022* (2014.02); *A61B 17/32* (2013.01); *A61M 1/0058* (2013.01);
(Continued)

(58) Field of Classification Search
CPC .. A61M 3/022; A61M 3/0254; A61M 3/0258; A61M 1/0058; A61M 1/0062; A61B 17/31
See application file for complete search history.

(56) References Cited

U.S. PATENT DOCUMENTS 5,091,656 A   2/1992  Gahn
5,484,402 A   1/1996  Saravia et al.
(Continued)

FOREIGN PATENT DOCUMENTS

CN   101035578     9/2007
JP   2001506509    5/2001
(Continued)

OTHER PUBLICATIONS

"Smith & Nephew introduces the Dyonics access 15 arthroscopic fluid irrigation system offering superior efficiency and ease of use at an affordable price", Copyright 2008 PR Newswire Europe Limited, www.prnewswire.co.uk/cgi/news/release?id41706 . . . , printed on Jun. 23, 2008. (1 page).
(Continued)

*Primary Examiner* — Edelmira Bosques
(74) *Attorney, Agent, or Firm* — Dicke, Billig & Czaja, PLLC (57) ABSTRACT A surgical fluid manager includes a pump releasably engageable to tubing and a user interface. The user interface is configured to enable finger-touch selection of a fluid flow rate through the tubing and configured to operate in at least one of a first mode or a second mode. In the first mode, the flow rate is controlled via direct selection of one of a plurality of selectable digital numeric values, while in the second mode the flow rate is controlled via user selection of one alphanumeric identifier within a scale of alphanumeric identifiers. Each respective alphanumeric identifier directly corresponds to just one instrument size within a scale of instrument sizes.

12 Claims, 5 Drawing Sheets

(51) Int. Cl.
*A61B 17/32* (2006.01)
*A61B 17/00* (2006.01)

(52) U.S. Cl.
CPC ........ *A61M 1/0062* (2013.01); *A61M 3/0254* (2013.01); *A61M 3/0258* (2013.01); *A61B 17/32002* (2013.01); *A61B 2017/00199* (2013.01); *A61B 2017/00212* (2013.01); *A61B 2017/00225* (2013.01); *A61M 2205/3334* (2013.01); *A61M 2205/3569* (2013.01); *A61M 2205/3592* (2013.01); *A61M 2205/502* (2013.01); *A61M 2205/505* (2013.01)

(56) References Cited

U.S. PATENT DOCUMENTS

| | | |
|---|---|---|
| 5,573,515 A | 11/1996 | Wilson et al. |
| 5,669,876 A | 9/1997 | Schechter et al. |
| 5,685,821 A * | 11/1997 | Pike .................. A61B 1/00039 600/118 |
| 5,800,383 A | 9/1998 | Chandler et al. |
| 5,810,765 A | 9/1998 | Oda |
| 5,882,339 A | 3/1999 | Beiser et al. |
| 5,931,808 A | 8/1999 | Pike |
| 6,086,598 A | 7/2000 | Appelbaum et al. |
| 6,162,194 A | 12/2000 | Shipp |
| 6,269,340 B1 | 7/2001 | Ford et al. |
| 6,780,166 B2 | 8/2004 | Kanda et al. |
| 6,899,697 B2 | 5/2005 | Fowler et al. |
| 7,150,713 B2 | 12/2006 | Shener et al. |
| 7,678,070 B2 | 3/2010 | Kumar et al. |
| 2003/0212379 A1 | 11/2003 | Bylund et al. |
| 2005/0209621 A1 | 9/2005 | Gordon et al. |
| 2006/0064053 A1 | 3/2006 | Bollish et al. |
| 2007/0078370 A1 | 4/2007 | Shener et al. |
| 2007/0233003 A1 | 10/2007 | Radgowski et al. |
| 2008/0154184 A1 | 6/2008 | Blight et al. |

FOREIGN PATENT DOCUMENTS

| | | |
|---|---|---|
| JP | 2002529185 | 9/2002 |
| JP | 2008513142 | 5/2008 |
| WO | 1998002205 | 1/1998 |
| WO | 2006059189 | 6/2006 |

OTHER PUBLICATIONS

"Baxter/Travenol Flo-Gard 6201 IV Pump", www.cnamedical.com/baxter_6201.html, printed on Jul. 10, 2008. (1 page).

"Intelijet and Access 15 Systems", www.endo.smith-nephew.com/fr/node.asp?NodeId=3629 . . . , printed on Jul. 10, 2008. (4 pages).

"InteliJET—Arthroscopic Fluid Management System", Copyright 2008 Alanis Semiconductor, www.alanissemi.com/intelijet.html, printed on Jul. 10, 2008. (1 page).

"Smith & Nephew—Ordering Information", http://global.smith-nephew.com/us . . . , printed on Jun. 23, 2008/ (6 pages).

* cited by examiner

SURGICAL FLUID MANAGEMENT SYSTEM

CROSS-REFERENCE TO RELATED APPLICATIONS

This Utility Patent Application is a Divisional application of U.S. patent application Ser. No. 12/196,777, entitled SURGICAL FLUID MANAGEMENT, filed Aug. 22, 2008, incorporated by reference herein.

BACKGROUND

The present disclosure relates to fluid management systems. In particular, it relates to fluid management systems for medical appliances, such as a surgical instrument.

Certain surgical appliances use a supply of fluid to irrigate a treatment site on a patient and/or to cool the surgical appliance. Some non-limiting examples of these types of surgical appliances include micro-debriders, otologic drills, suction-irrigator instruments and the like. One common method of providing consistent fluid delivery to a surgical appliance includes pumping fluid from a fluid source, such as a bag, through medical tubing via a positive displacement pump, such as a peristaltic pump. Peristaltic pumps are desirable for many reasons, such as their ability to maintain sterility of the fluid and cleanliness of the pump because the fluid flows through the medical tubing and does not come into contact with components of the pump. In use, tubing is placed within the peristaltic pump to allow its rollers to cyclically engage the tubing to provide the desired pumping action.

Another more traditional method of controlling the flow rate through the irrigation pathway includes a gravity-feed arrangement and the use of the ubiquitous, finger-operated, roller-pinch valve. By causing varying degrees of a pinching action on the tubing, this roller valve effectively controls the fluid flow rate. While simple to implement, this method suffers from a lack of consistency and a lack of predictability of the flow rate. In particular, a surgeon can waste much valuable time during surgery adjusting (or directing a nurses/technician to adjust) the flow rate via the roller valve to achieve a desired flow rate among different instruments within a single surgery. Moreover, from one surgery to another, the surgeon (or assisting nurse/technician) cannot readily predict which position of the roller valve will achieve the desired flow rate. Besides the time-consuming nature of this adjustment method, this variability in controlling the flow rate can be distracting for the surgeon or nurse/technician, which is typically monitoring a host of other instruments and physiologic parameters of the patient.

Accordingly, conventional fluid delivery systems can hamper surgical procedures by failing to provide consistent and predictable control of a fluid flow rate from surgery-to-surgery or from instrument-to-instrument within a single surgery.

DETAILED DESCRIPTION

Embodiments of the present disclosure are directed to controlling fluid flow through tubing to a medical appliance, such as a surgical instrument. In general terms, embodiments of the present disclosure can be used to provide controlled fluid delivery to any medical appliance receiving fluids via medical tubing. Accordingly, embodiments of the invention are not limited solely to use with surgical appliances, but can be employed with a wide variety of medical appliances.

Among other features and configurations, some embodiments of the present disclosure provide for a method of performing surgery that includes locating both a first surgical instrument and a fluid manager within or adjacent to a sterile field. In some embodiments, the fluid manager includes a console external to the sterile field and a remote control (in electrical communication with the console) within the sterile field. In some embodiments, one or both of the console and remote control comprise an electronic touchpad while in other embodiments, one or both of the console and remote control comprise an array of buttons, wheels, or other electromechanical tools for implementing and adjusting fluid flow control features of the fluid manager.

A flow rate is selected as an independent variable via the fluid manager. A surgical procedure is performed using the first surgical instrument, including directing an irrigation fluid (from a pump located external to the sterile field) at the flow rate into the tubing and through the irrigation conduit of the first surgical instrument. The irrigation conduit is arranged to direct a fluid onto the treatment site and/or to cool a cutting tool of the first surgical instrument. It is understood that in some instances, the treatment site is a diagnostic site in which no procedure is performed, while in other instances, a procedure or surgery is performed at the treatment site.

As noted above, in some embodiments, the remote control of the fluid manager is located within the sterile field during the procedure. This feature allows the surgeon to retain direct control over the flow rate of the irrigation fluid at the treatment site without necessarily requiring the assistance of a nurse or other technician.

In some embodiments, the flow rate is selected and displayed at the fluid manager via digital numeric values. However, in other embodiments, the flow rate is selected via an alphanumeric identifier which is displayed at the console and which corresponds to a preset flow rate. In still other embodiments, the flow rate is selected via one or more icons (which corresponds to a preset flow rate) and then displayed via alphanumeric identifiers at the console.

In one aspect, the alphanumeric identifier represents a size of the surgical instrument removably connected to the fluid manager. Accordingly, a surgeon can achieve the proper flow rate for a particular sized instrument by merely selecting, at the fluid manager (via the console or the remote control), an alphanumeric identifier that corresponds to the size of the surgical instrument. In this way, the surgeon need not memorize each of the separate flow rates that corresponds to a particular size of the surgical instrument nor must the surgeon rely on the expertise of the nurse to operate a conventional finger-operated pinch valve.

Moreover, the fluid manager stores data expressing a scaled relationship between a range of preset flow rates and a range of successively-larger sized or successively smaller-sized surgical instruments. In another aspect, the respective flow rates within the range are separated by a discrete interval.

Accordingly, during a procedure involving a suction-irrigator tool, when the surgeon chooses to replace the first sized tool with a second, differently sized tool, the surgeon can conveniently use the fluid manager to select the alphanumeric identifier corresponding to the size of the second tool to select the proper flow rate for the procedure. Alternatively, during a procedure involving a cutting-irrigator tool, when the surgeon chooses a tool or replaces a tool, the surgeon can conveniently use the fluid manager to precisely set a flow rate according to a digital numerical value. In either case, the selections can be made via the console (of the fluid manager) external to the sterile field or can be made via the remote control (of the fluid manager) positionable within the sterile field (to allow the surgeon to make the selections directly themselves). It also understood that references herein to a first tool do not necessarily correspond to a tool initially used in a procedure but that the terms first tool and second tool merely refer to the relative order of two tools used at some point during a procedure.

In this way, embodiments of the present disclosure enable a surgeon to achieve and maintain a consistent, predictable fluid flow rate during a surgical procedure.

These embodiments, and other embodiments, are described more fully in association with FIGS. 1-6.

Figure 1:
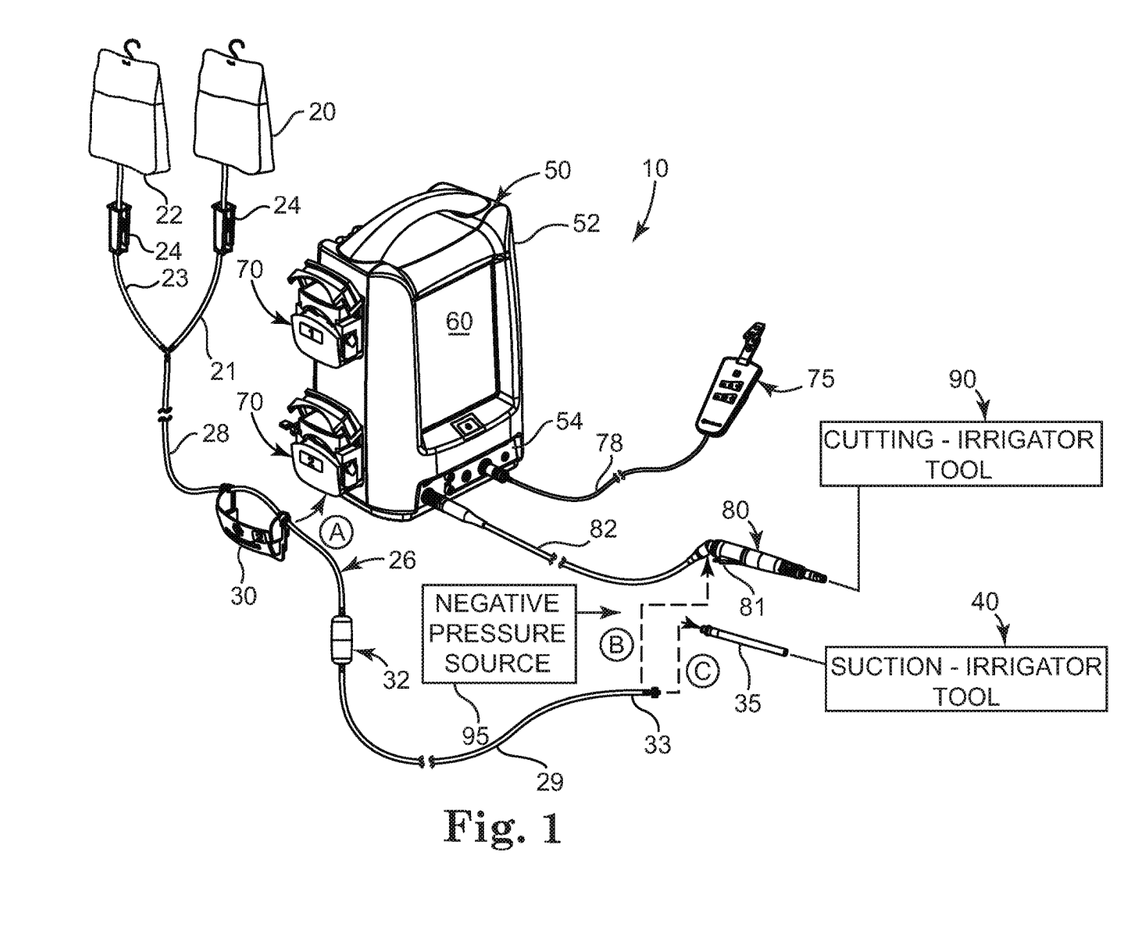
FIG. 1 is perspective view of a system for delivering fluid to a surgical instrument, in accordance with principles of the present disclosure.

A surgical system 10 is shown in FIG. 1, in accordance with principles of the present disclosure, and includes a mechanism for irrigating a treatment site or cooling a cutting tool of a surgical instrument. Among other features, the system 10 includes a fluid source (e.g., containers 20, 22), tubing set 26, loading cassette 30, console 50, pump assemblies 70, and surgical instruments such as cutting-irrigator tool 90 and suction-irrigator tool 40 (schematically represented in FIG. 1). Fluid stored in containers 20, 22 is supplied via the tubing portions 21, 23 for pumping via one of pump assemblies 70 through tubing set 26 to surgical instrument 40 or 90, as controlled by console 50. Each tubing portion 21, 23 includes a roller-pinch valve 24 adapted to initiate or terminate a gravity-fed transport of fluid out of containers 20, 22. In one aspect, each tubing portion 21, 23 is removably, fluidly connected to proximal portion 28 of tubing set 26 while distal portion 29 of tubing set 26 extends to and is fluidly connected to a fluid port 81 of cutting-irrigator tool 90 or to a fluid port of suction-irrigator tool 40 (via adapter 35). It is understood that embodiments of the present disclosure are not limited to the particular set instruments described but extend to a wider range of surgical instruments.

In general terms, with this arrangement, an irrigation pathway is established from containers 20, 22 through tubing portions 21, 23, through proximal portion 28 and distal portion 29 of tubing set 26, and into an irrigation conduit of one of the respective tools 40, 90.

In another aspect, the pump assemblies 70 are mounted onto the frame 52 of console 50 and in some embodiments, are releasably secured relative to the console 50 to allow convenient replacement of one or more of the pump assemblies 70. In one embodiment, each pump assembly 70 comprises a positive displacement pump having substantially the same features as, or similar features to, a Series 313 or 314 Peristaltic Pump available from Watson-Marlow Bredel Pumps Limited of Cornwall, United Kingdom. In other embodiments, the pump comprises a pressurized canister pump, a diaphragm pump, or other suitable pump for controlled fluid flow.

In one embodiment, each tubing set 26 includes a loading cassette 30 adapted to facilitate convenient and proper loading of the proximal portion 28 of tubing set 26 into releasable engagement relative to the peristaltic pumping mechanism of one of the pump assemblies 70. Once proximal portion 28 of tubing set 26 is installed via cassette 30, the rollers of the peristaltic mechanism of pump assembly 76 releasably engage the exterior of the tubing to squeeze or pump the fluid through the tubing. Among other features, proper loading via cassette 30 insures longevity of the tubing and enables predictable, consistent fluid flow through the tubing. This arrangement, and interaction of, the cassette 30, tubing set 26, pump assembly 70, and console 50 is further disclosed in the assignee's co-pending application Ser. No. 12/036,148, entitled METHOD AND SYSTEM OF LOADING OF TUBING INTO A PUMPING DEVICE, filed Feb. 22, 2008, and which is hereby incorporated by reference in its entirety. However, it is further understood that proximal portion 28 of tubing set 26 can be loaded onto one of the pump assemblies 70 using techniques for loading tools other than cassette 30.

In some embodiments, tubing set 26 additionally comprises a dampening mechanism 32 located in the distal portion 29 of tubing set 26 (i.e. distal of the loading cassette 30) so that dampening mechanism 32 is located distally of the peristaltic pumping action of pump assemblies 70. In one aspect, the dampening mechanism 32 acts to minimize pulsations in the fluid flow that results from the peristaltic pumping action. This arrangement smoothes the flow of the fluid as it moves through the irrigation pathway without substantially affecting the fluid flow rate. Nevertheless, in other embodiments, tubing set 26 omits a dampening mechanism 32 where pulsations in the fluid flow are not of concern.

In another aspect, by providing dampening mechanism 32 as part of tubing set 26, the dampening mechanism 32 is separate and independent from pump assembly 70. This arrangement, in turn, allows the operator to determine whether or not they would like to employ the smoothing action of the dampening mechanism 32 at the time they select a tubing set. Moreover, by providing dampening mechanism 32 as part of tubing set 26, pumping assemblies 70 and/or console 50 are unencumbered by a more complex conventional accumulator or dampening mechanism.

As further illustrated in FIG. 1, distal end 33 of tubing set 26 is removably connectable (as represented by directional arrow B) to fluid port 81 of handpiece 80 for fluidic connection to a surgical instrument, such as a cutting-irrigator tool 90. Alternatively, distal end 33 of tubing set 26 is removably connectable (as represented by directional arrow C) to a fluid port of another surgical instrument, such as a suction-irrigator tool 40, via adapter 35. In other embodiments, the tubing set 26 could be connected to the surgical instrument without using an adapter.

During a surgical procedure, an operator typically uses a cutting-irrigator tool 90 in one hand with the other hand manipulating a suction tool. Alternatively, during a procedure the operator uses a drill in one hand and a suction-irrigator tool 40 in the other hand. In either case, the connection of the distal end 33 of tubing set 26 to one of the tools 40, 90 provides an irrigation pathway to deliver the fluid for irrigation of the treatment site and/or to cool a cutting tool.

As further illustrated in FIG. 1, cutting-irrigator tool 90 is supported by handpiece 80 that is removably connectable to port station 54 of console 50. Via port station 54, console 50 supplies handpiece 80 with power and with control signals to operate a blade or bur of cutting-irrigator tool 90, as well as providing control signals for controlling the pump assemblies 70 to control the flow rate through the irrigation pathway.

Finally, console 50 includes a user interface 60 configured to provide control over a fluid flow rate via directing control signals to pump assemblies 70 and configured to control a cutting action or suction action at the respective surgical instruments 40, 90. In one aspect, user interface 60 is a graphical user interface including electronic touchpad capabilities which provide for simultaneous display of and/or activation of a particular function or feature via the touch of a finger, as further described in association with FIG. 2.

As further illustrated in FIG. 1, in some embodiments system 10 additionally comprises a remote control 75 removably connected (via line 78) to port station 54 of console 50. In other embodiments, remote control 75 wirelessly communicates with console 50 using RF or infrared communication protocols. As further described later in association with FIG. 2, in cooperation with console 50, remote control 75 is configured to control the fluid flow through tubing set 26 and to suction-irrigator tool 40 or to cutting-irrigator tool 90. In one embodiment, remote control 75 includes an electronic control touchpad configured to allow activation of a particular function or feature via the touch of a finger, and which may or may not include a graphical display associated with the particular function or feature.

In some embodiments, a kit of adapters is provided to quickly connect or link distal end 33 of tubing set 26 to suction-irrigator tool 40. In one embodiment, adapter 35 provides the link from tubing set 26 to suction-irrigator tool 40.

In another aspect, system 10 includes a negative pressure source 95 configured to be removably connectable to a suction-irrigator tool 40 to provide a suction or vacuum at the treatment site. Because a wide variety of tools can be used to employ suction, system 10 is not limited strictly to use of the suction-irrigator tool 40 to provide a suction function during a surgical procedure.

Figure 2:
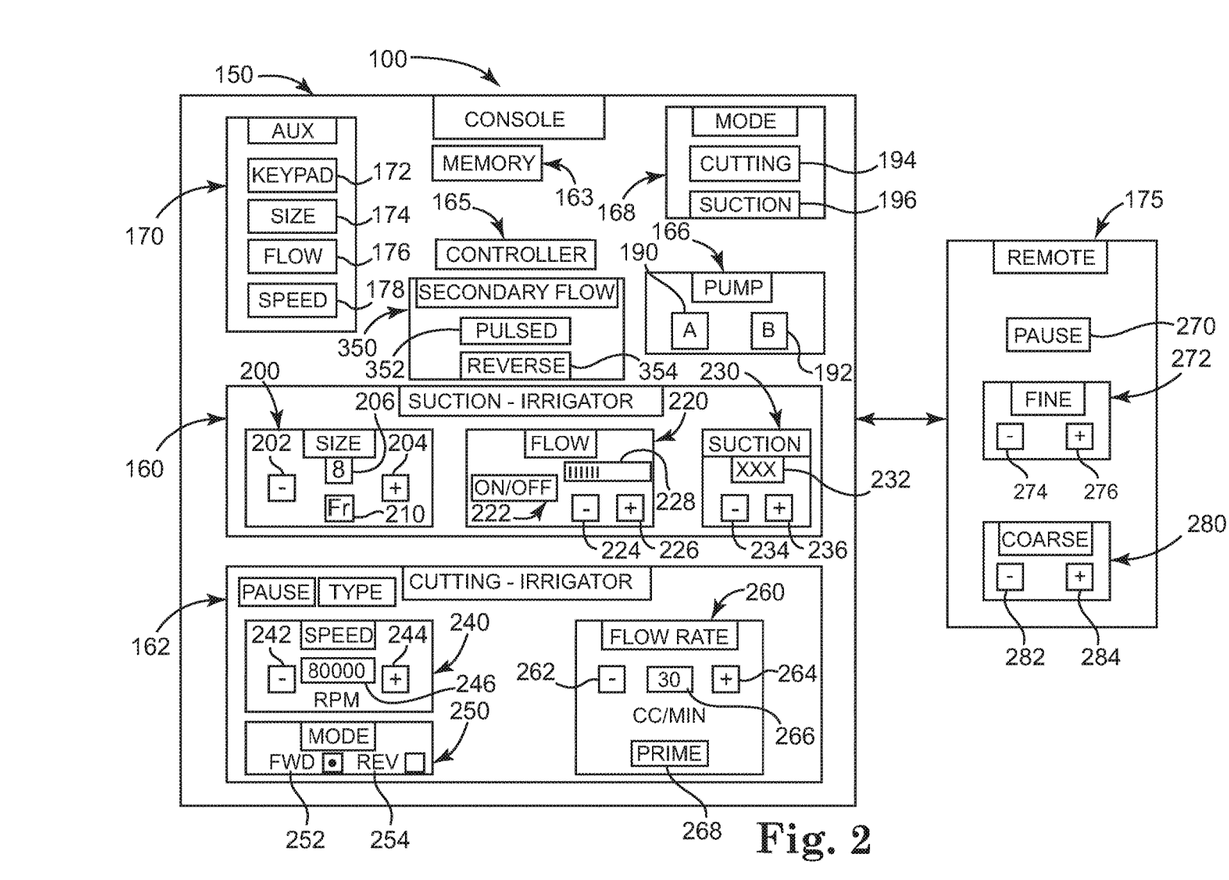
FIG. 2 is a schematic illustration including a block diagram of a fluid manager, in accordance with principles of the present disclosure.

With the above general construction of system 10 in mind, a fluid manager 100 is illustrated in FIG. 2. It is understood that the features and components of the fluid manager 100 can be arranged in many different forms and groupings. However, in the illustrated embodiment, fluid manager 100 includes a least a console 150 and a remote control 175 that communicates (wired or wirelessly) with console 150. In one aspect, the wireless communication is performed via RF, infrared communication protocols, or other known short range wireless communication protocols.

In one embodiment, fluid manager 100 comprises substantially the same features and attributes as console 50 and remote control 75 of FIG. 1 and further comprises the additional features and attributes described and illustrated in association with FIG. 2. In one embodiment, the features and components of console 150 are provided via a graphical user interface 60 (FIG. 1) providing electronic control touchpad features, and as such, console 150 provides for simultaneous display and/or activation of the functions and features presented in FIG. 2. In other embodiments, console 150 includes one or more thumbwheels, buttons, or other electromechanical control mechanisms for implementing the functions of the fluid manager 100.

In one embodiment, as shown in FIG. 2, console 150 includes a suction-irrigator module 160, a cutting-irrigator module 162, memory 163, controller 165, a pump selector 166, a mode selector 168, an auxiliary control module 170, and/or a secondary fluid control module 350.

In one embodiment, controller 165 comprises one or more processing units and associated memories configured to generate control signals directing the operation of fluid manager 100 of system 10, including control of at least console 150 and pump assemblies 70. In particular, in response to or based upon commands received via user interface 60 (as graphically represented by console 150 of FIG. 2) and/or instructions contained in the memory 163 associated with controller 165, controller 165 generates control signals directing operation of pump assembly 70 to selectively control the flow rate through the irrigation pathway provided by tubing set 26 and the irrigation conduit.

In some embodiments, remote control 175 is a passive device and is not controlled by controller 165. Instead, remote control 175 provides signals from within the sterile field to command the controller 165 of console 150 which is outside the sterile field. In some embodiments, remote control 175 comprises a switched resistor array while in other embodiments, the remote control 175 comprises capacitive switching, inductive switching, or a combination of capacitive, inductive, and/or resistive switching.

For purposes of this application, in reference to the controller 165 the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage, as represented by memory 163. In other embodiments, hard wired circuitry may be used in place of or in combination with software instructions to implement the functions described. For example, controller 165 may be embodied as part of one or more application-specific integrated circuits (ASICs). Unless otherwise specifically noted, the controller is not limited to any specific combination of hardware circuitry and software, nor limited to any particular source for the instructions executed by the processing unit.

In general terms, the suction-irrigator module 160 is configured to enable selection of a flow rate through tubing set 26 (FIG. 1) and through the irrigation conduit of a surgical tool (such as the later described suction-irrigator tool 400 shown in FIG. 5) for release onto a treatment site. In one embodiment, the suction-irrigator module 160 includes a device size selector 200, a micro flow adjuster 220, and a suction module 230.

In one aspect, the device size selector 200 is configured to select a flow rate according to a size of the device removably connected to the console 150. In a non-limiting example, the size of the device may be identified by its cross-sectional area or its outer diameter. The device size selector 200 includes various controls, such as a decrease function 202, an increase function 204, a display 206, and a unit function 210. In use, an operator manipulates increase function 204 or the decrease function 202 to achieve selection of the desired alphanumeric identifier setting, which is displayed at display 206. In the example shown, the device size selector 200 employs the French catheter scale, and therefore display 206, in combination with unit function 210, displays the alphanumeric identifier 8 Fr.

It is also understood that other embodiments, the alphanumeric identifier may be expressed solely as letters (e.g., A, B, C) to identify a particular size of instrument, while in yet other embodiments, other combinations of letters and numerals (e.g., A3, A4, etc.) are used to identify a particular size of instrument. Accordingly, the alphanumeric identifier may be an arbitrary representation relative to the size of the instrument or alternatively may be an indirect expression of the size of the instrument. In either case, the alphanumeric identifier does not reveal the preset flow rate for any particular sized instrument.

In still other embodiments, icons and/or types of graphical indicators are displayable and activatable via device size selector 200 (instead of alphanumeric identifiers) to select the size of the instrument from among a range of sizes and thereby indirectly select the fluid flow rate from among a range of different fluid flow rates. Like the previously described alphanumeric identifiers, the icons and/or other graphical indicators may be an arbitrary representation relative to the size of the instrument or alternatively may be an indirect expression of the size of the instrument. In either case, the icon (or other graphical indicator) does not reveal the preset flow rate for any particular sized instrument.

It is further understood that device size selector 200 is not limited to identifying instrument sizes via the French catheter scale, but extends to other units of measure available to identify relative sizing among a family of instruments. In one aspect, device size selector 200 is configured to identify one cross-sectional size within a scale of cross-sectional sizes of a single type of instrument. In turn, this one cross-sectional size directly corresponds to a particular flow rate within a scale of flow rates that provide the proper amount of irrigation at the treatment site (or cooling of a cutting tool) for that single type of instrument and a particular type of procedure.

Accordingly, it will be apparent to one skilled in the art that this alphanumeric identifier setting (viewable via display 206) does not indicate the flow rate for the surgical instrument (e.g., suction-irrigator tool 40 or cutting-irrigator tool 90) that is connected to console 150. Instead, console 150 includes a pre-programmed data table within its memory 163 that provides a different preset flow rate for each of the different sizes of the surgical instrument (such as a suction-irrigator tool 40) with each different preset flow rate being uniquely identified by a different alphanumeric identifier. A graphical illustration of a relationship between the alphanumeric identifiers that identify the respective sizes of the suction-irrigator tools 40 and their associated preset flow rates is later described and illustrated further in association with FIGS. 3A-3B.

Accordingly, even though the console 150 does not display the actual flow rates setting, the operator need only make a selection of the size of the surgical instrument knowing that the console 150 will automatically select the proper flow rate. In this way, with only the touch of a single button (via device size selector 200) the operator can have confidence that the flow rate will be consistent from procedure-to-procedure for that sized surgical instrument. In some embodiments, console 150 is configured to additionally or alternatively display the preset flow rates associated with the selected device size.

In one aspect, the ability to select a flow rate for a surgical instrument by conveniently entering an alphanumeric identifier proves very useful in certain surgical procedures in which a series of successively larger or successively smaller surgical instruments are employed to gain access to a particular treatment site. In one non-limiting example, many ENT procedures began with a larger sized surgical instrument (e.g. a cutting tool) and then progress to use of successively smaller surgical instruments as further access is gained to the treatment site. One such cutting tool includes a cutting-irrigator tool including a blade or bur for providing a debriding action and an irrigation conduit providing irrigation fluid for cooling the cutting tool and irrigating the treatment site. As the progression occurs from the larger instruments to the smaller instruments, the console 150 provided in accordance with the principles of the present disclosure automatically selects the proper preset flow rate for each of the successively smaller instruments, as the operator indicates the size of the instrument via the touch of a finger at device size selector 200 of console 150.

Figure 3A:
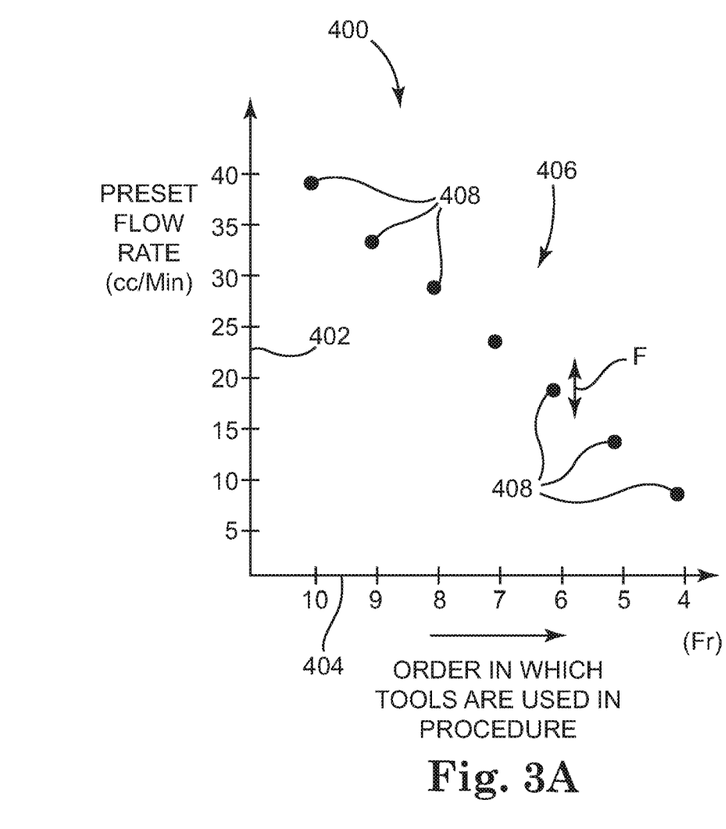
FIG. 3A is a graph schematically illustrating a scaled relationship of preset flow rates and a progression of successively smaller sizes of instruments, in accordance with principles of the present disclosure
Figure 3B:
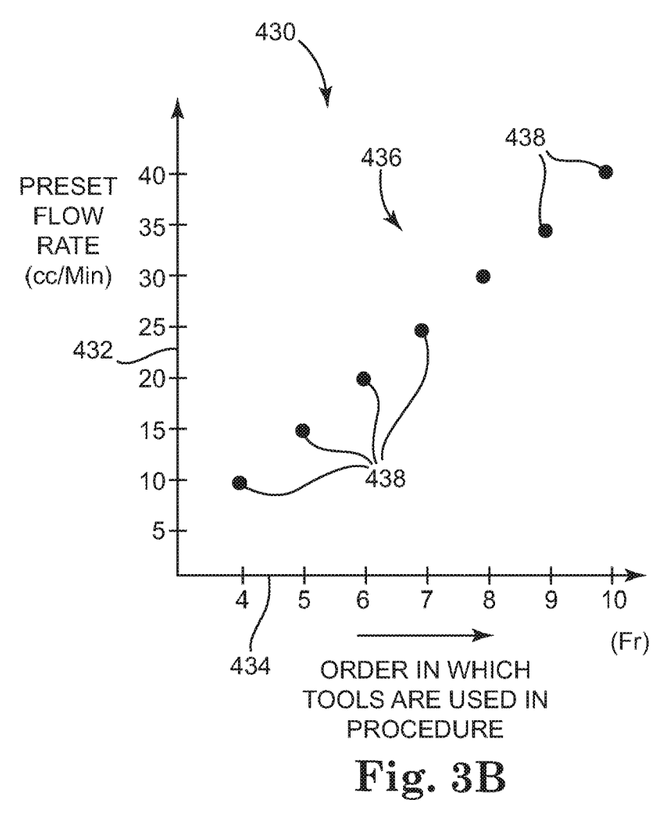
FIG. 3B is a graph schematically illustrating a scaled relationship of preset flow rates and a progression of successively larger sizes of instruments, in accordance with principles of the present disclosure

This relationship is further illustrated in association with FIGS. 3A and 3B, which schematically illustrates the scaled relationship between the plurality of preset flow rates and a range of sizes of surgical instruments associated with each of those respective flow rates. FIG. 3A provides a graph 400 schematically depicting a scale 406 of points 408. Each point 408 represents a particular size of a surgical instrument and a preset flow rate associated with that particular size. In one aspect, an x-axis 404 represents the order in which a series of surgical instruments are used in a single procedure. In some embodiments, the size of the surgical instruments is measured according to a French catheter scale, while in other embodiments, a different measurement unit or scale identifier is used. In another aspect, the y-axis 402 represents a preset flow rate of the fluid for a particular sized instrument.

It is also understood that the particular scale shown in FIG. 3A is merely illustrative and that embodiments of the present disclosure are not limited to the particular sizes of instruments or to the particular flow rates depicted in FIG. 3A. Nevertheless, in the example shown in FIG. 3A, scale 406 provides a preset flow rate of 40 cc/minute for a 10 French sized instrument, a preset flow rate of 35 cc/minute for a 9 French sized instrument, a preset flow rate of 30 cc/minute for an 8 French sized instrument, and so on. As further illustrated by FIG. 2, the successive flow rates are separated by discrete intervals (e.g., 5 cc/minute), so that the change in the flow rate for each differently sized instrument occurs in a stepwise fashion.

Among other relationships, graph 400 illustrates that the larger sized surgical instruments correspond to a larger preset flow rate such that the instruments used earlier in the procedure have higher flow rates and that as the size of the instruments used in succession progressively decrease in size, a corresponding decrease in each successive preset flow rate occurs. Because this scaled relationship of the flow rates and instrument sizes of graph 400 is stored in memory 163 of console 150 (FIG. 2), the system automatically sets the proper flow rate upon the operator indicating the size of the instrument (via the alphanumeric identifier of the device size selector 200).

It is also understood that the operator may alter the order in which the surgical instruments are used or may skip several sizes any time along the scale 406. Nevertheless, the operator will still quickly obtain the proper flow rate for the selected instrument due to the convenient selection mechanism provided via device size selector 200, which enables selection of the proper preset flow rate via direct selection of the size of the instrument by use of alphanumeric identifiers.

In a similar fashion, FIG. 3B illustrates a graph 430 depicting a scale 436 of discrete points 438 expressing a scaled relationship of preset flow rates (as represented by y-axis 432) and instrument sizes (as represented by x-axis 434). In one aspect, graph 430 comprises substantially the same features and attributes of graph 400 of FIG. 3A except that, in this embodiment, the order in which the instruments are used corresponds to a procedure in which successively larger instruments are used throughout the progression of the surgical procedure (as represented by the x-axis 434). Otherwise, graph 430 is substantially similar to graph 400 and illustrates a series of points 438 that represents a plurality of preset flow rates separated by discrete intervals with each preset flow rate directly corresponding to a particular sized surgical instrument.

Referring again to FIG. 2, in addition to saving time for the operator, as well as ensuring a predictable, consistent flow rate for a particular size device from procedure-to-procedure, the automatically selectable flow rate also ensures a proper proportion between the flow rate and the amount of suction for a particular sized instrument. Moreover as illustrated in FIG. 2, in some embodiments, a suction module 230 is provided to enable adjustments to increase (via an increase function 236) or decrease (via a decrease function 234) the amount of suction at treatment site via the suction-irrigator tool 40. A display 232 may be provided to track the relative increase or decrease in the level of suction.

In the case of a progression of successively smaller instruments, a relatively smaller amount of suction will be provided for each smaller sized instrument so that the amount of suction stays in proportion to the relatively smaller flow rate of irrigation provided at the treatment site for each successively smaller sized instrument. In the case of a progression of successively larger instruments, a relatively larger amount of suction will be provided for each larger sized instrument so that the amount of suction stays in proportion to the relatively larger flow rate of irrigation provided at treatment site for each of successively larger sized instrument. Finally, in another aspect, even when an operator skips around between different sizes of instruments (instead of following a size-by size progression) the appropriate amount of suction will be provided to the particular instrument.

In the event that the operator desires a slightly higher or slightly lower irrigation flow rate, micro flow adjuster 220 enables fine-tuning of the flow rate selected by device size selector 200. In particular, micro flow adjuster 220 includes an on/off button 222, a decrease button 224, an increase button 226, and an adjustment display 228. The on/off button 222 is configured to enable control over the initiation of, or termination of, the flow of irrigation fluid via console 150. The decrease button 224 and the increase button 226 enable small decreases and small increases, respectively, away from the macro or basic flow rate set by the device size selector 200. Display 228 provides a graphical indication of the relative increase or decrease in the macro flow rate. In one aspect, this fine tuning adjustment of a preset flow rate for a particular instrument is illustrated in FIG. 3A via directional arrow F, which illustrates a small range of increase or decrease from a pre-selected flow rate (e.g. 20 cc/min) for a 6 French sized surgical instrument.

In some embodiments, each touch of the decrease button 224 or the increase button 226 of the micro flow adjuster 220 causes a respective decrease or increase having a value at least one order of magnitude less than an order of magnitude of the increase or decrease in the flow rate caused by each touch of the decrease button 202 or the increase button 204 of the device size selector 200 (i.e., a macro flow adjuster). In one non-limiting example, buttons 224, 226 of micro flow adjuster 220 enable a respective decrease or increase of 5% or 10% a nominal flow rate (one of the macro flow rates selected via device size selector 200).

In other embodiments, each touch of the decrease button 224 or the increase button 226 of the micro flow adjuster 220 causes a respective preset decrease or preset increase that is some fraction or percentage (e.g. 1%, 2%, 5%, 7%, 10%, or 15%) of the increase or decrease in the flow rate caused by each touch of the decrease button 202 or the increase button 204 of the device size selector 200 (i.e., a macro flow adjuster).

In this way, the operator can make small changes or adjustments to the preset flow rate (selected via the alphanumeric identifier of device size selector 200) that corresponds to the size of the surgical instrument in use. Accordingly, the operator gains the advantages of a predictable preset flow rate matched to the size of the surgical instrument while still retaining the flexibility of adjusting the flow rate up or down from a preset flow rate.

In some embodiments, console 150 also comprises a cutting-irrigator module 162 as illustrated in the FIG. 2. This module 162 includes a cutting speed module 240, a directional mode selector 250, and a flow rate module 260. The cutting speed module 240 includes an increase function 244, a decrease function 242, and a display 246. The increase function 244 and the decrease function 242 enable selection and adjustments of the speed of a cutting tool, as typically measured in revolutions per minute (RPM). The directional mode selector 250 enables selection of a forward mode or a reverse mode of the cutting tool via the respective forward function 252 or the reverse function 254. In addition, it is understood that cutting-irrigator module 162 (generally or via directional mode selector 250) also optionally provides selection to other cutting modes, such as an oscillation cutting mode.

In another aspect, flow rate module 260 of cutting-irrigator module 162 provides a decrease function 262 and an increase function 264 to select a flow rate as a digital numerical value as displayed at display 266. In the non-limiting example shown, the flow rate is displayed in cc/minute units. By making the flow rate selectable as a digital numerical value, the surgeon can readily achieve a predictable flow rate which can be reproduced from instrument-to-instrument within a procedure, or from surgery-to-surgery.

In one embodiment, the flow rate is selected as an independent variable. In other words, the flow rate is not dependent upon another variable such as a fluid pressure within a joint (such as an arthroscopic surgery). Accordingly, once set, the flow rate is not free to vary (unless specifically adjusted to a new constant rate via console 150) below or up to a limit, as occurs in various conventional arthroscopic surgery systems.

In some environments, the flow rate module 260 also includes a prime function 268 configured to ready an irrigation conduit for cooling a cutting tool or irrigating a treatment site. As noted above, it is understood that the term treatment site generally refers to a diagnostic site, a surgical site, an irrigation site, or combinations thereof.

In further reference to FIG. 2, in some embodiments, fluid manager 100 also includes a remote control 175 which is sized and adapted for location within a sterile field during a procedure. In one aspect, remote-control includes a pause function 270, a fine adjustment function 272, and a coarse adjustment function 280. The pause function 270 enables the operator to initiate, terminate or suspend a flow of fluid through the irrigation conduit of one of the respective tools 40, 90. In one embodiment, the pause function 270 is used to control priming or flushing of the irrigation conduit of one of the respective tools 40, 90 (FIG. 1).

The coarse adjustment function 280 includes a decrease function 282 and an increase function 284. In one aspect, when the suction-irrigator module 160 is in use with a suction-irrigator tool 40 (FIG. 1) or 400 (FIG. 5), the coarse adjustment function 280 of remote-control 175 functions as a device size selector, substantially similar to the device size selector 200 of suction-irrigator module 160 (FIG. 2). Accordingly, the decrease function 282 and the increase function 284 of remote-control 175 causes a respective decrease or increase in a selection of a size of the instrument by the alphanumeric identifiers selectable via device size selector 200 of console 150. In this way, a surgeon can use a remote control 175 to achieve a proper preset flow rate by merely identifying the size of the instrument to be used.

On the other hand, when the cutting-irrigator module 162 is in use with a cutting-irrigator tool 90 (FIG. 1) or 300 (FIG. 4), the coarse adjustment function 280 of remote-control 175 enables direct selection of a flow rate according to a digital numeric value in a manner substantially the same as flow rate selector 260 of cutting-irrigator module 162 (FIG. 2). Accordingly, the decrease function 282 and the increase function 284 of remote-control 175 causes a respective decrease or increase in the flow rate as selected by and represented via a digital numeric value.

In another aspect, the fine adjustment function 272 of remote-control 175 enables small increases and decreases in a selected flow rate. For example, when the suction-irrigator module 160 is in use, a small increase in a flow rate made via increase button 276 of remote-control 175 corresponds to a small increase made via increase button 226 of micro flow adjuster 220 of console 150 (FIG. 2). Likewise a small decrease in the flow rate made a decrease button 274 of remote-control 175 corresponds to a small decrease made via decrease button 224 of micro flow adjuster 220 of console 150 (FIG. 2). On the other hand, when the cutting-irrigator module 162 is in use, changes made via the decrease button 274 and the increase button 276 of remote-control 175 correspond to small decreases and increases, respectively, of the base flow rate selected via flow rate selector 260 of console 150.

In one embodiment, the remote control 175 also can be used to control the speed and direction of a cutting tool or drill, such as tool 90. In this arrangement, the remote control 175 operates in an auxiliary mode in which the coarse adjustment function 280 is used to control the direction of the drill with activation of the increase function 284 of the coarse adjustment function 280 (of remote control 175) causing a forward drill direction and activation of the decrease function 282 of the coarse adjustment function 280 causing a reverse drill direction. In addition, with the remote control 175 operating in this auxiliary mode, the fine adjustment function 272 of remote control 175 is used to control the speed of the drill with the increase function 274 causing in an increase in the speed and the decrease function 276 causing a decrease in the speed of the drill. In some embodiments, in this auxiliary mode of remote control 175, the pause function 270 of the remote control 175 is used to reverse the direction (e.g., forward, reverse) of the drill.

In some embodiments, an additional set of an increase function and a decrease function are added to the remote control 175 (in a manner substantially similar to the coarse adjustment function 280 of FIG. 2) to allow the remote control 175 to apply controls to both the fluid flow and the drill at the same time. In this other embodiments, the operator can toggle between using the remote control 175 to control of the drill or to control the fluid flow.

Console 150 also comprises a mode selector 168 including a cutting function 194 to enable the operator to select fluid management via cutting-irrigator module 162 for a cutting-irrigator tool 90 while suction function 196 enables the operator to select fluid management via suction-irrigator module 160 for the suction-irrigator tool 40. In some embodiments, both the suction-irrigator module 160 and the cutting-irrigator module 162 will be displayed simultaneously on user interface 60 of console 150, regardless of which function 194, 196 is selected. On the other hand, in other embodiments, just one of suction-irrigator module 160 or cutting-irrigator module 162 is displayed at a time on console 150 with the mode selector 168 determining which of the respective modules 160, 162 is displayed. In this latter arrangement, console 150 is convertible between use with suction-irrigator module 160 or with cutting-irrigator module 162.

In some embodiments, console 150 includes pump selector 166, as illustrated in FIG. 2. The pump selector 166 comprises buttons 190, 192 for selecting activation of one or both of the pump assemblies 70 as is appropriate depending upon which fluid containers 20, 22 or other fluid sources are in use.

Referring again to FIG. 2, in some embodiments, console 150 includes auxiliary control module 170, which is configured to provide an alternate mechanism to set a flow rate for a surgical instrument. This embodiment may prove particularly useful for those users which are more comfortable with or familiar with keypad entry of various values and/or functions, instead of using the suction-irrigator module 160 or the cutting-irrigator module 162. With this in mind, the auxiliary control module 170 includes a keypad 172 configured to allow the entry of digital numeric values as well as alphanumeric identifiers. A size function 174 of the auxiliary control module 170 enables a user such as a surgeon to enter a size of the instrument via keypad 172 using an alphanumeric identifier to thereby cause an appropriate flow rate for irrigation fluid to travel into (and through) the irrigation conduit of the particular instrument. In another aspect, the flow function 176 of the ancillary control module 170 enables the surgeon to directly enter the requested flow rate (for an irrigation conduit of a particular surgical instrument) as a digital numeric value using keypad 172. In yet another aspect, the speed function 178 of auxiliary control module 170 enables the surgeon (or their assistant) to directly enter a rotational speed of a cutting tool of the surgical instrument via keypad 172 instead of using the speed selector 240 of cutting-irrigator module 162. Finally, values entered and/or functions selected via auxiliary control module 170 can be displayed on the console via a display like any one or more of the respective displays 206, 228, 246, and 266 of console 150, as well other display mechanisms forming part of a graphical user interface such as, graphical user interface 60 of console 50.

In some embodiments, console 150 of fluid manager 100 also includes additional fluid control modes provided via secondary fluid control module 350 to augment control of fluid flow in addition to selection of the fluid flow rate. As illustrated in FIG. 2, secondary flow control module 350 comprises a pulsed flow function 352 and a reverse flow function 354. In use, a fluid flow rate is selected via one or more of the mechanisms of the fluid manager 100 (FIG. 2), as previously described. Thereafter, one of the pulsed flow function 352 and/or reverse flow function 354 is selected for use to better implement the selected flow rate.

In one embodiment, the pulsed flow function 352 causes pulsed fluid flow to enable a single nozzle/orifice size of an irrigation conduit to deliver an irrigant stream over a wider flow range and provides better surgical sight visibility in at least two ways. First, pulsing the fluid flow via the pulsed flow function 352 interrupts a continuous fluid stream into the treatment site that can otherwise block a surgeon's vision. Second, pulsing the fluid flow provides intermittent no-flow intervals, thereby allowing the surgeon to apply suction at the treatment site (during the no-flow interval) to remove any pooled irrigation fluid that could otherwise obstruct the surgeon's view of the anatomy at the treatment site.

In one non-limiting example, assuming that a flow rate of 20 cc/minute were selected, the pulsed flow function 352 would maintain an average flow rate of 20 cc/minute via intermittent pulses of a substantially greater rate of fluid flow (e.g., 50 cc/minute) separated by intervals of no fluid flow. Accordingly, when applying the pulsed fluid flow, the same total volume of fluid is directed to the treatment site for period of time (e.g., a minute) as a non-pulsed fluid flow rate. However, with the pulsed fluid function, several time no-flow intervals separate successive pulses of fluid flow enabling the greater visibility of the treatment site and the opportunity for applying suction without ongoing fluid flow.

In one embodiment, upon its activation at console 150 the reverse flow function 354 is automatically applied each time that the surgeon selectively stops a flow of irrigation fluid. Accordingly, in addition to the standard stopping action of the pump assembly 70, the reverse flow function 354 causes the pump assembly 70 to additionally implement a brief reversal of the ongoing, forward fluid flow to a direction of fluid flow away from the treatment site. This brief reversal is sufficient to offset the momentum of the forward fluid flow and depressurizes the dampening mechanism 32 (FIG. 1) to enable a faster flow response upon a user request to start and stop fluid flow. In another aspect, the reverse flow function 354 also promptly stops any ongoing fluid flow through the tubing (and irrigation conduit), thereby allowing removal (via suction) of any pooled irrigation fluid at the treatment site while simultaneously preventing dripping from the distal end of the irrigation conduit that could otherwise obstruct a surgeon's view of small anatomy. In other words, the reverse flow function 354 is tantamount to a stop-quickly function with drip prevention. Accordingly, once activated, the reverse flow function 354 is applied automatically each time flow is selectively stopped, regardless of whether the suction-irrigator tool 40 or the cutting-irrigator tool 90 is being used by the surgeon. For example, during use of the suction-irrigator tool 40, fluid flow is selectively stopped by manually pressing the pause button on the remote control 175 or on the console, which thereby automatically triggers application of the reverse flow function 354. In another example, during use of the cutting-irrigator tool 90, each time the drill of the cutting-irrigator tool 90 is stopped (via a foot pedal release or other stopping mechanism), the fluid flow is also automatically stopped according to the reverse flow function 354.

Figures 4, 5:
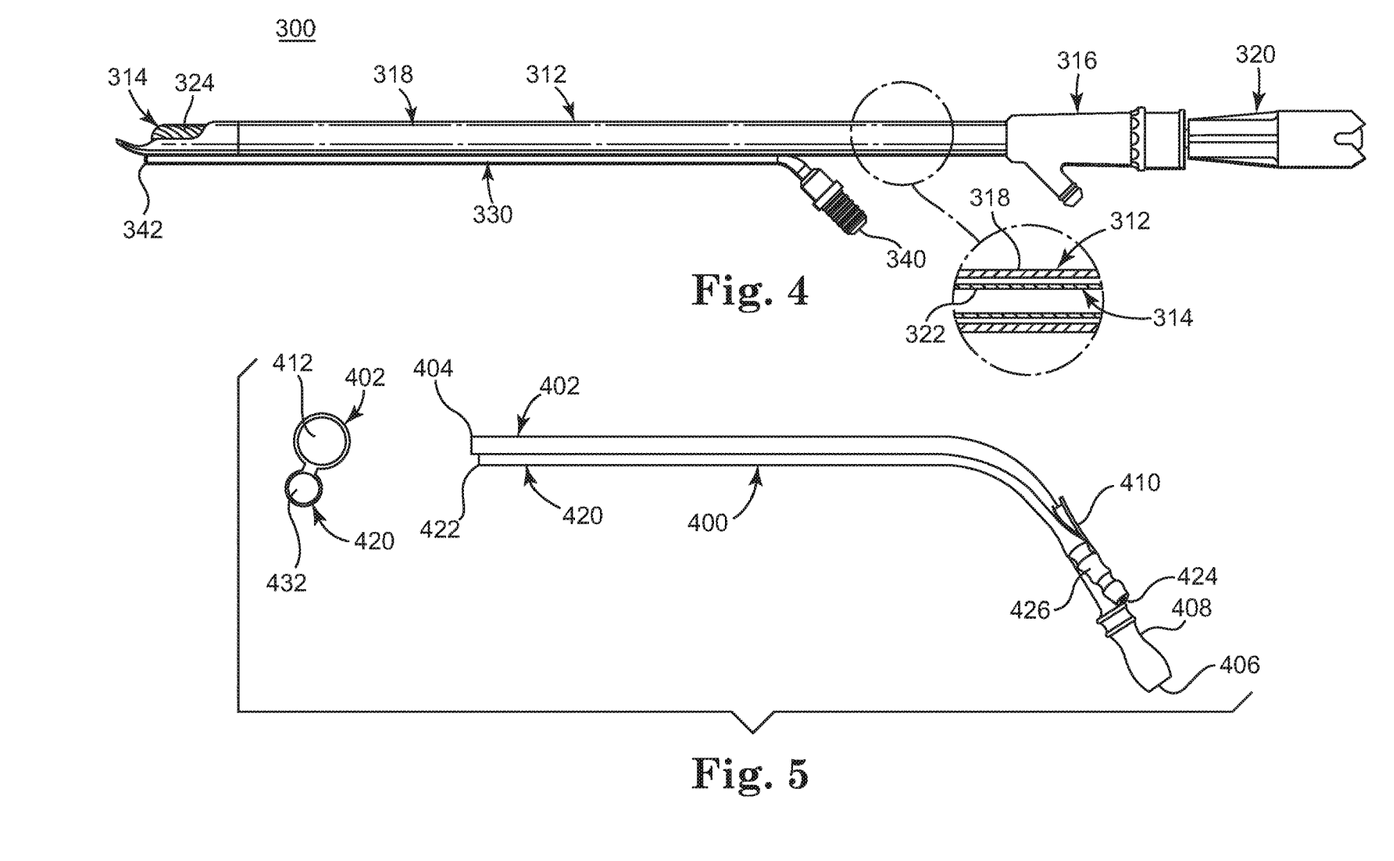
FIG. 4 is a side plan view of a cutting-irrigator instrument, in accordance with principles of the present disclosure.
FIG. 5 is a side plan view of a suction-irrigator instrument, in accordance with principles of the present disclosure.

While the surgical instrument used in conjunction with the fluid manager 100 of FIG. 2 can take many shapes and forms, one particular surgical instrument adapted for use with the cutting-irrigator module 162 comprises a cutting-irrigator tool such as a micro-burring instrument 300, as illustrated in FIG. 4. The micro-burring instrument 300 is configured to optimally perform a sinus surgical procedure, for example a septoplasty or turbinoplasty procedure. However it is understood that the principles of the present disclosure extend to other types of cutting-irrigator tools and other types of surgeries—both sinus and non-sinus.

As shown in FIG. 4, the instrument 300 includes an outer tubular assembly 312 and an inner tubular assembly 314 (referenced generally in FIG. 1). The outer tubular assembly 312 includes an outer hub 316 and an outer tubular member 318, whereas the inner tubular assembly 314 includes an inner hub 320, and an inner tubular member 322. The inner tubular member 322 is sized to be coaxially received within the outer tubular member 318 and forms a bur 324 at its distal end. The outer tubular member 318 extends distally from the outer hub 316 while the outer hub 316 can assume a wide variety of forms known in the art. With this in mind, both inner hub 320 and outer hub 316 are configured for engagement with reciprocating components of a hand piece (e.g. handpiece e.g. in FIG. 1), which, in turn, controls high-speed rotation of inner tubular member 322 relative to outer tubular member 318. This arrangement ultimately results in the high-speed rotation of bur 324, which acts to de-bride or cut target tissue at a treatment site.

Additionally, and in one embodiment, cutting instrument 300 includes an irrigation tube 330 that is exteriorly secured to the outer tubular member 318. The irrigation tube 330 is configured to convey an irrigation fluid to a working tip of the instrument 300, thereby cooling bur 324 and irrigating the surrounding treatment site. In this one configuration shown in FIG. 4, a connector 340 is provided at one end of the irrigation tube 330 and is adapted to fluidly connect the irrigation tube 330 with a fluid source, such as one of the fluid sources 20, 22 in FIG. 1. An opposite, distal end 342 of the irrigation tube 330 is arranged to convey fluid through a wall of the outer tubular member 318 to irrigate bur 324 and the surrounding treatment site. Alternatively, the outer tubular assembly 312 can be adapted to internally deliver irrigation fluid via the outer tubular member 318 to cool bur 324 and to irrigate the surrounding treatment site.

FIG. 5 illustrates a suction-irrigator tool in accordance with the principles of the present disclosure and which can be provided for use as the suction-irrigator tool 40 shown in FIG. 1. While a suction-irrigator tool can take many forms, in this embodiment, a suction-irrigator instrument 400 comprises a suction portion 402 and an irrigation portion 420. The suction portion 402 defines a suction conduit 412 extending between a distal end 404 and a proximal end 406. A connection portion 408 is defined at the proximal end 406 and is configured for connection to a negative pressure source 95 (FIG. 1) via tubing. The amount of suction is controlled via conventional techniques, such as aperture portion 410 of suction portion 402, and/or via the suction module 230 of suction-irrigator module 160 of console 150 of FIG. 2. On the other hand, the irrigation portion 420 defines an irrigation conduit 432 extending between a distal end 422 and a proximal end 424. A connection portion 426 is defined at the proximal end 424 and is configured for connection to distal portion 29 of tubing set 26 via one or more adapters, such as adapter 35 shown in FIG. 1. In this way, irrigation portion 420 forms part of the irrigation pathway extending from fluid containers 20, 22 and tubing set 26.

Figure 6:
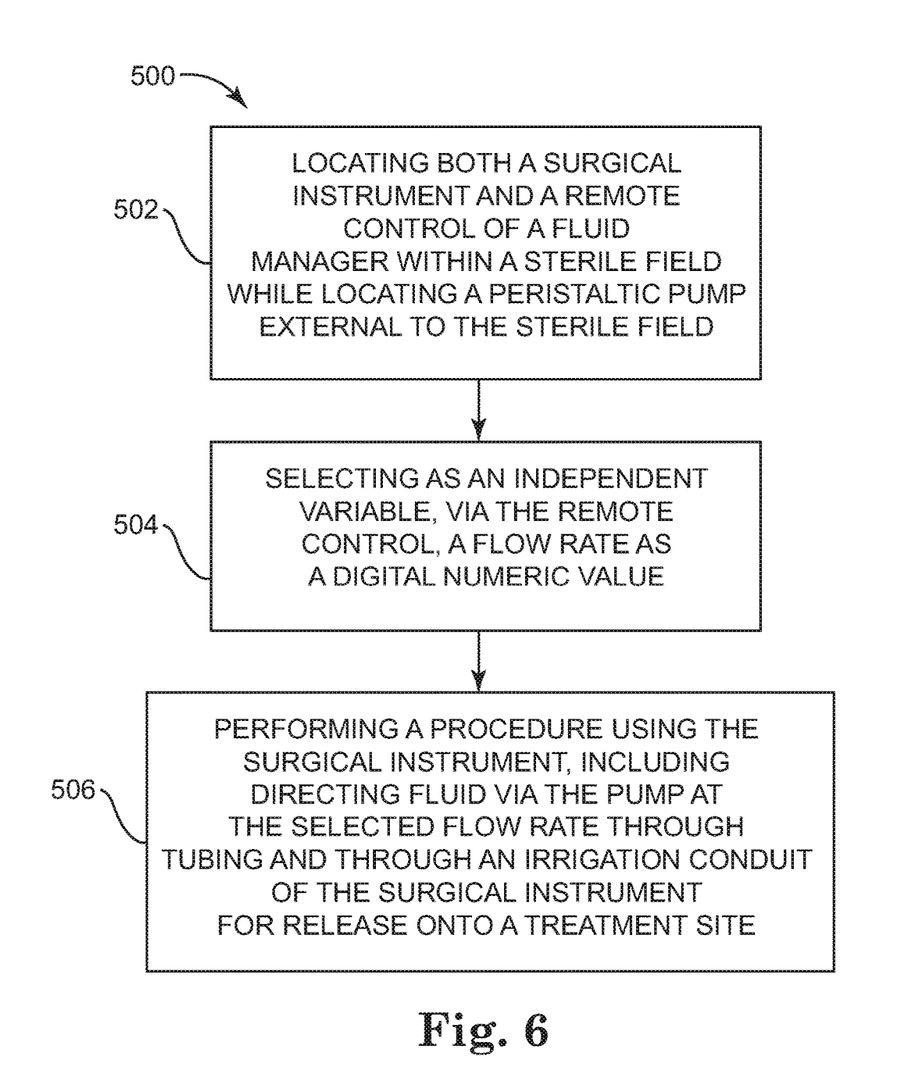
FIG. 6 is a flow diagram schematically illustrating a method of managing an irrigation fluid during a medical procedure, in accordance with principles of the present disclosure.

FIG. 6 provides a flow diagram that schematically illustrates a method 500 of surgery in accordance with the principles of the present disclosure. In one embodiment, method 500 employs one or more of the systems or components previously described in association with FIGS. 1-5 while in other embodiments method 500 is performed using other systems or components.

As illustrated in FIG. 6, the method comprises locating both a surgical instrument and a remote control of a fluid manager within a sterile field while locating a peristaltic pump external to the sterile field as shown at block 502. At block 504, via the remote control, the first flow rate is selected as an independent variable expressed as a digital numeric value. The method continues with performing a procedure using the surgical instrument including directing fluid, via the pump at the selected first flow rate, through tubing and through an irrigation conduit of the surgical instrument for release onto a cutting tip (such as bur 324 in FIG. 4) and/or onto a treatment site.

Embodiments of the present disclosure provide a system and method in which operator can choose a preset flow rate to be assured of a consistent, predictable flow rate of irrigation fluid at the treatment site, whether the surgical instrument is a cutting-irrigator tool or a suction-irrigator tool. In one non-limiting example, finger-touch selection of an instrument size via an alphanumeric identifier causes selection of a flow rate within a scale of preset flow rates. In another example, a preset flow rate is selected as an independent variable and represented via in a digital numeric value on a display. Moreover, with the available remote control feature, the surgeon can readily select such a preset flow rate (directly via a digital numeric value or via selection of an instrument size) or make small adjustments in the flow rate remotely within the sterile field by the simple touch of a button.

Although the present disclosure has been described with reference to preferred embodiments, workers skilled in the art will recognize that changes can be made in form and detail without departing from the spirit and scope of the present disclosure.

What is claimed is:

1. A method of performing surgery comprising:
locating both a first surgical instrument and a remote control of a fluid manager within a sterile field while locating a peristaltic pump external to the sterile field;
selecting as an independent variable, via the remote control, a first fluid flow rate as a digital numeric value; and
performing a surgical procedure using the first surgical instrument, including directing the irrigation fluid through tubing, via the peristaltic pump at the first fluid flow rate, and through the irrigation conduit of the first surgical instrument onto the treatment site.

2. The method of claim 1 comprising:
arranging the fluid manager to receive user selection of an increase or a decrease in the selected first fluid flow rate by a numeric value via discrete intervals of at least one order of magnitude less than the order of magnitude of the selected first fluid flow rate.

3. The method of claim 1 comprising:
changing the selected first fluid flow rate via discrete intervals in correspondence with performing a surgical procedure using at least one of successively larger surgical instruments or successively smaller surgical instruments throughout the procedure.

4. The method of claim 1 comprising:
arranging the first surgical instrument to include at least one of:
a suction conduit independent and separate from the irrigation conduit; or
a cutting element.

5. The method of claim 1, comprising:
selectively terminating a flow of the irrigation fluid through the irrigation conduit, including temporarily reversing a direction of the fluid flow.

6. The method of claim 5, wherein temporarily reversing the direction of the fluid flow comprises:
decreasing dampening, at a location between the pump and the irrigation conduit of the surgical instrument, to enable faster fluid flow response.

7. A method comprising:
locating both a first surgical instrument and a remote control of a fluid manager within a sterile field while locating a pump external to the sterile field;
selecting as an independent variable, via the remote control, a first fluid flow rate as a digital numeric value;
performing a surgical procedure using the first surgical instrument, including directing an irrigation fluid through tubing, via the pump at the first fluid flow rate, and through an irrigation conduit of the first surgical instrument onto the treatment site;
providing a plurality of selectable surgical instruments which range in cross-sectional size according to a scale defined by a discrete interval between successive sizes within the range of cross-sectional sizes, wherein the plurality of instruments include at least the first surgical instrument and a differently sized, second surgical instrument;
providing a plurality of selectable fluid flow rates, including at least the first fluid flow rate and a second fluid flow rate, represented by a plurality of alphanumeric identifiers wherein each respective fluid flow rate is calibrated to directly correspond to the cross-sectional size of one of the respective selectable surgical instruments; and
selecting one of the respective fluid flow rates, via the remote control within the sterile field, by selecting one of the alphanumeric identifiers corresponding to the cross-sectional size of the second surgical instrument.

8. The method of claim 7, comprising:
replacing the first surgical instrument with the second surgical instrument; and
resuming the procedure using the second surgical instrument, including directing the irrigation fluid via the pump at the second fluid flow rate through the tubing and through the irrigation conduit of the second surgical instrument.

9. A method comprising:
locating both a first surgical instrument and a remote control of a fluid manager within a sterile field while locating a pump external to the sterile field;
selecting as an independent variable, via the remote control, a first flow rate as a digital numeric value; and
performing a surgical procedure using the first surgical instrument, including directing the irrigation fluid through tubing, via the pump at the first fluid flow rate, and through the irrigation conduit of the first surgical instrument onto the treatment site; and
implementing the selected first fluid flow rate as an average flow rate via a series of pulses in which each individual pulse directs the irrigation fluid at a second fluid flow rate substantially greater than the average flow rate and wherein the respective pulses are separated from each other by no-flow intervals in which no fluid exits the irrigation conduit onto the treatment site.

10. The method of claim 9, comprising:

performing suction at the treatment site during the no-flow intervals.

11. A method comprising:

locating both a first surgical instrument and a remote control of a fluid manager within a sterile field while locating a pump external to the sterile field;

selecting as an independent variable, via the remote control, a first fluid flow rate as a digital numeric value;

performing a surgical procedure using the first surgical instrument, including directing the irrigation fluid through the tubing, via the pump at the first fluid flow rate, and through the irrigation conduit of the first surgical instrument onto the treatment site; and arranging the fluid manager to enable electronic finger-touch selection of a fluid flow rate through the tubing and through the first surgical instrument, including configuring an user interface configured to operate convertibly between a first mode in which the selectable fluid flow rate, including the first fluid flow rate, is controllable via user selection of one of a plurality of selectable digital numeric values and a second mode in which the flow rate is controllable via user selection of one alphanumeric identifier within a scale of alphanumeric identifiers wherein each respective alphanumeric identifier directly corresponds to just one instrument size within a scale of instrument sizes.

12. The method of claim 11, comprising:

arranging the user interface to include the remote control and a console positionable external to the sterile field and supporting the pump;

arranging the remote control to be in communication with the console and positionable within the sterile field, wherein the remote control is separate from and independent of the surgical instrument; and arranging both the console and the remote control to provide the electronic finger-touch selection of the selectable fluid flow rate via one of the respective first and second modes.

* * * * *